United States Patent
Ferencic et al.

(10) Patent No.: US 12,121,582 B2
(45) Date of Patent: Oct. 22, 2024

(54) INJECTABLE PHARMACEUTICAL FORMULATIONS OF LEFAMULIN

(71) Applicant: NABRIVA THERAPEUTICS GMBH, Vienna (AT)

(72) Inventors: Mathias Ferencic, Klosterneuburg (AT); Werner Heilmayer, Zillingtal (AT); Peter Hinsmann, Vienna (AT); Wolfgang Wicha, Bruck an der Leitha (AT)

(73) Assignee: NABRIVA THERAPEUTICS GMBH, Wein (AT)

( * ) Notice: Subject to any disclaimer, the term of this patent is extended or adjusted under 35 U.S.C. 154(b) by 0 days.

(21) Appl. No.: 15/736,865

(22) PCT Filed: Jun. 14, 2016

(86) PCT No.: PCT/EP2016/063609
§ 371 (c)(1),
(2) Date: Dec. 15, 2017

(87) PCT Pub. No.: WO2016/202788
PCT Pub. Date: Dec. 22, 2016

(65) Prior Publication Data
US 2018/0360966 A1    Dec. 20, 2018

Related U.S. Application Data

(60) Provisional application No. 62/180,871, filed on Jun. 17, 2015.

(51) Int. Cl.
| | | |
|---|---|---|
| *A61K 47/12* | (2006.01) | |
| *A61K 9/00* | (2006.01) | |
| *A61K 9/08* | (2006.01) | |
| *A61K 31/215* | (2006.01) | |
| *A61K 47/02* | (2006.01) | |
| *A61K 47/26* | (2006.01) | |

(52) U.S. Cl.
CPC ........... *A61K 47/12* (2013.01); *A61K 9/0019* (2013.01); *A61K 9/08* (2013.01); *A61K 31/215* (2013.01); *A61K 47/02* (2013.01); *A61K 47/26* (2013.01)

(58) Field of Classification Search
CPC ...... A61K 31/215; A61K 47/02; A61K 47/12; A61K 47/26; A61K 9/0019; A61K 9/08; A61P 31/04
USPC ........................................................ 514/550
See application file for complete search history.

(56) References Cited

U.S. PATENT DOCUMENTS

| | | | |
|---|---|---|---|
| 4,130,709 A | 12/1978 | Nagarajan | |
| 5,164,405 A * | 11/1992 | McFarlane | A61K 9/0019 514/354 |
| 6,187,746 B1 | 2/2001 | Conrath et al. | |
| 6,972,297 B2 | 12/2005 | Brooks et al. | |
| 7,790,767 B2 * | 9/2010 | Mang | A61P 31/04 514/530 |
| 8,071,643 B2 | 12/2011 | Mang et al. | |
| 8,153,689 B2 * | 4/2012 | Mang | C07D 295/096 514/529 |
| 8,222,447 B2 * | 7/2012 | Mang | A61P 17/10 560/125 |
| 9,120,727 B2 * | 9/2015 | Riedl | C07C 319/20 |
| 10,913,703 B2 * | 2/2021 | Heilmayer | C07C 69/013 |
| 2003/0114674 A1 | 6/2003 | Brooks et al. | |
| 2003/0162831 A1 | 8/2003 | Ascher et al. | |
| 2010/0035987 A1 | 2/2010 | Mang et al. | |
| 2010/0331812 A1 * | 12/2010 | Friden | A61K 31/437 604/501 |
| 2013/0040954 A1 * | 2/2013 | Mang | C07D 295/096 514/239.5 |

(Continued)

FOREIGN PATENT DOCUMENTS

| | | |
|---|---|---|
| CN | 1427827 A | 7/2003 |
| DE | 4023848 A1 | 1/1992 |

(Continued)

OTHER PUBLICATIONS

David Sek (Research Scientist, Pfizer, Issue 3, Jul. 10, 2012, pp. 1-11< Breaking the habits: Moving away from commonly used buffers in pharmaceuticals—European Pharmaceutical Review).*

(Continued)

*Primary Examiner* — Adam C Milligan
*Assistant Examiner* — Amanda Michelle Petritsch
(74) *Attorney, Agent, or Firm* — Venable LLP

(57) ABSTRACT

The present invention relates to an injectable pharmaceutical formulation comprising a compound of formula (I)

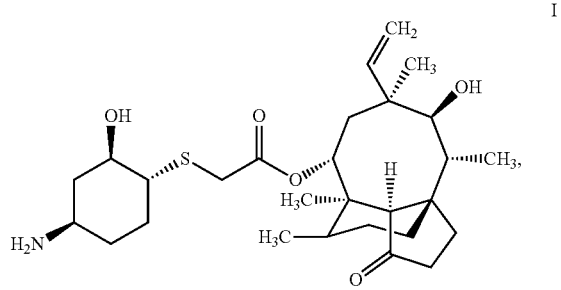

the formulation being buffered to a pharmaceutically acceptable pH-value, especially a pH-value of from 2 to 6, in particular a pH value of from 3 to 5.5, preferred a pH-value of about 4 to 5, particularly preferred about 5.

17 Claims, No Drawings

(56) References Cited

U.S. PATENT DOCUMENTS

| | | | | |
|---|---|---|---|---|
| 2013/0079400 | A1 | 3/2013 | Riedl et al. | |
| 2014/0256731 | A1* | 9/2014 | Mang | A61P 17/10 |
| | | | | 514/239.5 |
| 2017/0266194 | A1* | 9/2017 | Mang | A61K 31/5375 |
| 2020/0231529 | A1* | 7/2020 | Heilmayer | C07C 67/52 |

FOREIGN PATENT DOCUMENTS

| | | | | |
|---|---|---|---|---|
| JP | 2002508330 A | 3/2002 | | |
| WO | 99/30728 A1 | 6/1999 | | |
| WO | 01/74788 A1 | 10/2001 | | |
| WO | 0204414 A1 | 1/2002 | | |
| WO | 03082260 A2 | 10/2003 | | |
| WO | 03090740 A1 | 11/2003 | | |
| WO | WO-2004089886 A1 * | 10/2004 | | C07C 323/62 |
| WO | WO-2006070195 A1 * | 7/2006 | | C07D 401/014 |
| WO | 2007000004 A1 | 1/2007 | | |
| WO | 2007014409 A1 | 2/2007 | | |
| WO | 2008/113089 A1 | 9/2008 | | |
| WO | WO-2011146954 A1 * | 12/2011 | | A61K 31/215 |
| WO | WO-2014191109 A1 * | 12/2014 | | A61K 31/407 |

OTHER PUBLICATIONS

W.T. Prince, et al., "Phase II Clinical Study of BC-3781, a Pleuromutilin Antibiotic, in Treatment of Patients with Acute Bacterial Skin and Skin Structure Infections," Antimicrobial Agents and Chemotherapy, vol. 57, No. 5, pp. 2087-2094 (2013).
L. Willems, et al., "Itraconazole oral solution and intravenous formulations: a review of pharmacokinetics and pharmacodynamics," Journal of Clinical Pharmacy and Therapeutics, 26(3), pp. 159-169 (2001).
Y. Mehmood, et al., "Excipients Use in Parenteral and Lyophilized Formulation Development," Open Science Journal of Pharmacy and Pharmacology, 3(3), pp. 19-27 (2015).
R.G. Strickley, "Solubilizing Excipients in Oral and Injectable Formulations," Pharmaceutical Research, vol. 21, No. 2, pp. 201-230 (2004).
Clinical and Laboratory Standards Institute (CLSI, former NCCLS) Document M7-A7 vol. 26, No. 2: "Methods for Dilution Antimicrobial Susceptibility Tests for Bacteria that Grow Aerobically—Approved Standard; Seventh Edition" (Jan. 2006).
Clinical and Laboratory Standards Institute (CLSI, former NCCLS), Document, M11-A6, vol. 24, No. 2: "Methods for Antimicrobial Susceptibility Testing of Anaerobic Bacteria—Approved Standard; Sixth Edition" (2004).
Amburgey, J. et al., "Small Molecule Analogs of Phospholipid-Metal Ion Binding Sites: Synthesis and Molecular Modeling of Cyclohexane-1, 2, 4-triol Trisphosphates," Bioorganic Chemistry, 22, pp. 172-197 (1994).
Berner, H. et al., "Synthese AB-Trans-Anellierter Derivate DES Tricyclischen Diterpens Pieuromutilin Durch Intramolekulare 1,5-Hydrid-Verschiebung," Tetrahedron, Pergamon Press Ltd., Great Britain, vol. 36, No. 12-I, pp. 1807-1811 (1980).
Egger, H. et al., "New Pleuromutilin Derivatives with Enhanced Antimicrobial Activity," The Journal of Antibiotics, vol. XXIX, No. 9, pp. 915-927 (1976).
Gomez-Sanchez, E. et al., "Synthesis and Transformations of Alkyl N-(1-cyclohex-3-enyl)carbamates Prepared from Cyclohex-3-ene Carboxylic Acid via Curtius Rearrangement," Tetrahedron, vol. 61, pp. 1207-1219 (2005).
Kapferer, P. et al., "Electrophilic Bromination of N-Acylated Cyclohex-3-en-1-amines: Synthesis of 7-Azanorbornanes," Helvetica Chimica Acta, vol. 87, pp. 2764-2789 (2004).
Marvell, E. et al., "Products of Acetolysis of 3-(3-Cyclohexenyl)propyl and 4-(3-Cyclohexenyl_butyl p-Toluenesulfonates," Journal of Organic Chemistry, vol. 33, No. 7, pp. 2291-2993 (1968).
O'Brien P. et al., "cis- and trans-Stereoselective Epoxidation of N-Protected 2-Cyclohexen-1-ylamines," Organic Letters, vol. 5, No. 26, pp. 4955-4957 (2003).
Raju, B. et al., "Conformationally Restricted Analogs of Deoxynegamycin," Bioorganic & Medicinal Chemistry Letters, 14, pp. 3103-3107 (2004).
Vankar, Y. et al., "Chiral Acetals in Organic Synthesis: Regioselective Synthesis of 2-and 3-Hydroxy Acetals from 2,3-Olefinic Acetals. Reinvestigation and Further Applications," Tetrahedron, vol. 50, No. 7, pp. 11057-11078 (1994).
Zhang, L. et al., "Stereocontrolled Synthesis of Kelsoene by the Homo-Favorkii Rearrangement," Organic Letters, vol. 4, No. 21, pp. 3755-3758 (2002).
International Preliminary Report on Patentability for International Application No. PCT/EP2016/063609 dated Dec. 19, 2017 (7 pages).
G. Eichenbaum et al., "Methods to evaluate and improve the injection site tolerability of intravenous formulations prior to first-in-human testing", Journal of Pharmacological and Toxicological Methods, 68, pp. 394-406 (2013).
S.L. Gupta et al., "Parenteral Formulation Development of Renin Inhibitor Abbott-72517", J. Pharm. Sci. Technol., 48(2), pp. 86-91 (1994).
P. Simamora et al., "Studies in Phlebitis VIII: Evaluations of pH Solubilized Intravenous Dexverapamil Formulations", PDA J. of Pharm. Sci. Technol., 50(2), pp. 123-128 (1996).
The Merck Index, 12th Edition, Item 7694, p. 1298.
Novak, "Are pleuromutilin antibiotics finally fit for human use?", Ann. N.Y. Acad. Sci., 1241, pp. 71-81 (2011).
S.H. Yalkowsky et al., "Formulation-Related Problems Associated with Intravenous Drug Delivery", Journal of Pharmaceutical Sciences, 87(7), pp. 787-796 (1998).
R. Christoph, et al., "Pain Reduction in Local Anesthetic Administration Through pH Buffering", Annals of Emergency Medicine, 17(2), pp. 117-120 (1988).
J. Fransson, et al., "Local Tolerance of Subcutaneous Injections", J. Pharm. Pharmacol., 48, pp. 1012-1015 (1996).
Full Prescribing Information for XENLETA® Injection, revised Aug. 2019.
Full Prescribing Information for Cardine IV, revised Sep. 2010.

* cited by examiner

INJECTABLE PHARMACEUTICAL FORMULATIONS OF LEFAMULIN

The present application is a national-stage entry under 35 U.S.C. § 371 of International Patent Application No. PCT/EP2016/063609, filed Jun. 14, 2016, which claims the benefit to U.S. Provisional Application No. 62/180,871 filed Jun. 17, 2015, the entire disclosure of each of which is incorporated by reference herein.

BACKGROUND OF THE INVENTION

Field of the Invention

The present invention concerns pharmaceutical compositions comprising a compound of formula (I)

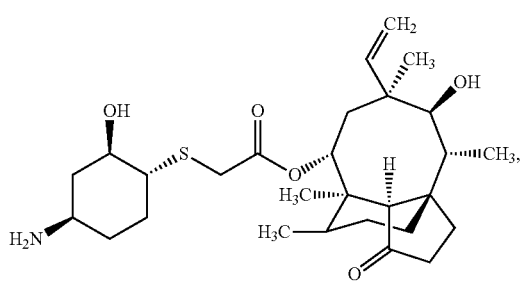

i.e. 14-O-{[(1R, 2R, 4R)-4-amino-2-hydroxy-cyclohexylsulfanyl]-acetyl}-mutilin (in the following referred to as "BC-3781") as well as salts thereof.

Pleuromutilin, a compound of formula

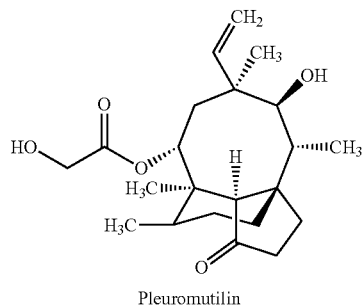 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin is a naturally occurring antibiotic, produced e.g. by the basidiomycetes *Pleurotus mutilus* and *P. passeckerianus*, see e.g. The Merck Index, 12th edition, item 7694.

A number of further pleuromutilins having the principle ring structure of pleuromutilin and being substituted at the primary hydroxy group have been developed, e.g. as antimicrobials. Due to their pronounced antimicrobial activity, a group of pleuromutilin derivatives, amino-hydroxy-substituted cyclohexylsulfanylacetylmutilins, as disclosed in WO 2008/113089, have been found to be of particular interest. As described in WO2008/113089 14-O-{[(4-Amino-2-hydroxy-cyclohexyl)-sulfanyl]-acetyl}-mutilins are particularly useful compounds because of their activity against Gram-positive and Gram-negative pathogens, especially in context of respiratory tract and skin and skin structure infections. In particular, 14-O-{[(1R, 2R, 4R)-4-amino-2-hydroxy-cyclohexylsulfanyl]-acetyl}-mutilin (in the following referred to as "BC-3781" or "lefamulin") has been developed for systemic use to treat serious infections in humans. BC-3781 has been inter alia described by R. Novak, Are pleuromutilin antibiotics finally fit for human use?, Ann. N.Y. Acad. Sci. 1241 (2011) 71-81 and W. T. Prince et al, Phase II Clinical Study of BC-3781, a Pleuromutilin Antibiotic, in Treatment of Patients with Acute Bacterial Skin and Skin Structure Infections, Antimicrobial Agents and Chemotherapy Vol 57, No 5 (2013), 2087-2094. The latter publication illustrates the first proof of concept of a pleuromutilin derivative to treat serious infections in humans via systemic administration. Lefamulin can be administered orally and intravenously. When compounds are administered intravenously, often injection site intolerabilities are observed. Infusion site irritations are often more pronounced when the compound is delivered as intraveneous infusion and can range from mild, to moderate and severe in the human setting. Local intolerance effects include pain, erythema and phlebitis. S. H. Yalkowsky et al, Journal of Pharmaceutical Sciences, Vol 87, No 7, 1998, 787 have described formulation related problems associated with intravenous drug delivery and report hemolysis, precipitation, phlebitis and pain as major adverse effects. However, no formulation or formulation development for pleuromutilins in general or lefamulin in particular are outlined in this prior art document.

G. Eichenbaum et al, Journal of Pharmacological and Toxicological Methods, 68, 2013, 394 have described methods to evaluate and improve the injection site tolerability of intravenous formulations prior to first-in-human testings for compounds with low solubility at physiological blood pH, e.g. pH 7.4. The investigation focused on model compound JNJ-X which is zwitter-ionic. BC-3781, however, is neither a zwitterion nor does it have low solubility at blood pH.

WO 1999/30728 describes injectable compositions containing dalfopristine/quinupristine in an aqueous solution in combination with an additive intended to avoid or reduce intolerance effects at the site of injection. The additives encompass buffer solutions. However, said document is related to the combinatorial application of dalfopristine/quinupristine which are two distinct compounds that are both very different in structure and physicochemical properties to pleuromutilin derivatives, e.g. BC-3781. Furthermore, BC-3781 is employed as single compound to treat serious infections inter alia caused by highly resistant pathogens.

Further prior art documents describe formulation development and studies for distinct molecules which are related to improvement of infusion site tolerability. A short noncomprehensive selection of such prior art is listed as follows:

a) S. Gupta et al, Parenteral Formulation Development of Renin Inhibitor Abbott-72517, J. of Pharm. Sci. & Tech. 48(2):86-91 (1994)

b) P. Simamora et al, "Studies in Phlebitis VIII: Evaluations of pH Solubilized Intravenous Dexverapamil Formulations", PDA J. of Pharm. Sci. & Tech. 50(2):123-128 (1996)

c) L. Willems et al, Itraconazole oral solution and intravenous formulations: a review of pharmacokinetics and pharmacodynamics, Journal of Clinical Pharmacy and Therapeutics, 2001, 26, 159.

All of the molecules described in these further prior art documents are very different from pleuromutilin derivatives in structure and physicochemical properties when compared to BC-3781. Therefore the task to develop formulations with improved local tolerance for lefamulin was very different to the approaches described in prior art.

This task is solved by the subject matter of claim 1. Preferred embodiments are listed in the dependent claims.

In particular, the present invention concerns injectable formulations of BC-3781, especially for intravenous administration.

BC-3781 and its synthesis are disclosed, for example, in WO 2008/113089.

It has been found that injectable formulations containing BC-3781 which are buffered to a pharmaceutically acceptable pH-value, especially a pH-value of from 2 to 6, in particular a pH value of from 3 to 5.5, preferred a pH-value of about 4 to 5, particularly preferred about 5, avoid or at least reduce intolerance effects, in particular at the site of injection.

Furthermore, it has been found that the buffer is preferably selected from the group consisting of citrate buffers, phosphate buffers and mixtures thereof. A preferred citrate buffer is prepared by mixing citric acid with trisodium citrate.

The amount of buffer, especially of a citrate buffer, within the formulation is preferably within a range of from 5 mM to 25 mM, preferably 8 mM to 20 mM, especially preferred about 10 mM to about 20 mM.

Most preferred is a 10 mM to 20 mM citrate buffer, especially a 10 mM citrate buffer, preferably used in clinical formulations in humans.

The remaining constituents of the injectable formulation as well as their respective amounts can be selected by the skilled artisan on the basis of the available general knowledge.

For example, an injectable formulation may be based on normal saline solution, containing 0.9% (w/v) NaCl (in the following also abbreviated as "NSS") or a solution of dextrose in water, such as 5% (w/v) (anhydrous) dextrose in water (in the following also abbreviated as "D5W").

A preferred composition is based on NSS and contains 10 mM citrate buffer to 20 mM citrate buffer, especially preferred 10 mM citrate buffer.

The amount of BC-3781 in the formulation may range from 100 mg/250 ml to 300 mg/250 ml solution, preferably about 150 mg/250 ml solution, calculated as BC-3781 in free base form.

BC-3781 may be employed for the preparation of injectable formulations according to the present invention in the form of a pharmaceutically acceptable salt, especially a crystalline salt.

Preferred crystalline salt forms of BC-3781 are disclosed e.g. in WO 2011/146954.

In one aspect of the present invention injectable formulations employ preferably acetate and/or L-lactate as pharmaceutical acceptable salts of BC-3781, most preferably acetate salt.

In a further aspect the present invention provides intravenous formulations which improve the local tolerability of BC-3781 after intravenous application, in particular after intravenous infusion.

The solubility of BC-3781 acetate in various media is as follows:

| Media | Solubility [mg/ml] |
|---|---|
| Water | ≥100 |
| 0.9% (w/v) saline | |
| pH 1 (0.1M HCl) | |

-continued

| Media | Solubility [mg/ml] |
|---|---|
| pH 6.8 (150 mM phosphate buffer) | |
| pH 7.4 (300 mM phosphate buffer) | ≥100 |

Reported local tolerability issues are often linked to insufficient solubility of the compound at physiological pH which, however, is not the case for BC-3781. Other issues causing local tolerance problems could be linked to stability issues of compounds at physiological pH (e.g. pH 6.8 to 7.4), which is—again—not the case for BC-3781 because excellent stability is observed at these pH ranges.

The pKa value measured of BC-3781 is 9.41, which means that at physiological pH most of the compound is ionized.

So the effect of improved tolerability of BC-3781 when delivered in the buffered formulations and formulation concepts described in this application is completely surprising.

In principle, a buffer solution is prepared as a combination of weak acids and their salts (sodium salts, etc.) or of weak alkalis and their salts.

In one aspect, formulations are prepared using an acid/base system in which at least one of the constituents is a weak acid or weak base whose pKa value is within the range of 2 to 6 and in which the resultant pH of the system is in the region of or below said pKa value.

The preferred pH range for formulations administered to humans is of from 3 to 5.5, more preferably of from 4 to 5, particularly preferred about 5. Further preferred pH ranges are from 4 to 6, preferably 5 to 6.

Even more preferably, the system can comprise one or more pharmaceutically acceptable weak organic or inorganic acids whose pKa value is within the range of from 2 to 6, combined with its conjugate base, with a strong base or with a weak base, or alternatively the system can comprise one or more pharmaceutically acceptable strong organic or inorganic acids, combined with at least one weak base belonging to an acid/base couple whose pKa value is within the range from 2 to 6.

The following acids (or their conjugate bases) are examples of acids which can form part of the composition of the system: citric acid, acetic acid, lactic acid, amino acids, malic acid, ascorbic acid, glutamic acid, benzoic acid, histidine, glutaric acid, propionic acid, succinic acid, formic acid, maleic acid, aspartic acid, malonic acid, gluconic acid, glucoheptonic acid, and phosphoric acid. These acids can be combined with their conjugate base, with the conjugate base of another weak acid or with sodium hydroxide. The conjugate bases of the acids mentioned above can also be combined, where appropriate, with methanesulphonic acid, hydrochloric acid, phosphoric acid or sulphuric acid.

Among these examples, given without any limitation being implied, the ones which are most particularly advantageous are citric acid, phosphoric acid and combinations of both and/or the conjugate bases thereof.

The resulting mixtures result in a buffered solution.

The buffered formulation according to the present invention may comprise a pharmaceutically acceptable vehicle, preferably selected from the group consisting of normal saline solution, 5% dextrose solution and mixtures thereof, most preferred normal saline.

Other pharmaceutical acceptable vehicles are inter alia aqueous solutions of 10% or 40% glucose, 20% Xylitol, lactated Ringer's solution (in the following also referred to as "LRS"), and mixtures thereof.

The final formulations of BC-3781 (pharmaceutically acceptable vehicle, buffers and BC-3781 salt optionally with adjuvants) will have a pharmaceutically acceptable osmolality, e.g. from 250 to 400 mosm/kg.

According to the present invention, the buffer solutions can be prepared according to known methods commonly used, in particular by adding sodium hydroxide to a predetermined amount of acid to reach the desired pH, which ranges from 2 to 6, followed by adding water to the desired volume.

In one aspect of the present invention, the buffered solution of BC-3781 can be established by reconstituting a 100 mM to 1000 mM buffer concentrate solution, preferably 200 mM to 800 mM, most preferred 250 mM to 540 mM, into a pharmaceutically acceptable intravenous vehicle and by adding BC-3781 preferentially as pharmaceutically acceptable salt, e.g. acetate salt (abbreviated in the following as .Ac) or L-lactate salt (abbreviated as .La) or adding a 1 mg/ml to 100 mg/ml, preferably 5 mg/l to 50 mg/ml, most preferably 10 mg/ml to 15 mg/ml solution of BC-3781 as pharmaceutically acceptable salt, e.g. acetate or L-lactate salt resulting in the final desired concentration of BC-3781.

In another aspect of the present invention, all ingredients of the formulation e.g. buffer components and BC-3781, preferably as pharmaceutically acceptable salt, can be added directly to a pharmaceutically acceptable intravenous vehicle.

In one aspect of the present invention, buffer systems include citrate buffer, phosphate buffer and acetate buffer, preferably citrate buffer and phosphate buffer or mixtures thereof, most preferably citrate buffer at a pH range between 3 to 6, preferably pH 4 to 6, most preferably pH 5.

The buffer systems can be prepared by dissolving an organic acid, e.g. citric and acetic acid, or an inorganic acid, e.g. phosphoric acid in water or preferably in a pharmaceutically acceptable intravenous vehicle and adjusting the pH with a base, preferably alkali base, e.g. KOH and NaOH, most preferably NaOH.

Alternatively a buffer system can be prepared by dissolving an organic acid, e.g. citric and acetic acid, or inorganic acid, e.g. phosphoric acid, with the appropriate conjugate base, e.g. trisodium citrate, sodium dihydrogen phosphate or sodium acetate, in water or preferably in a pharmaceutically acceptable intravenous vehicle. Optionally the pH can be (fine) adjusted to the final desired pH with hydrochloric acid or sodium hydroxide.

Optionally in addition to the tonicity agents which are preferably chosen in particular from glucose, sodium chloride, glycerol, sorbitol, mannitol, fructose or dextrans 40 and 70, in the buffered formulations the pharmaceutical compositions can contain a pharmaceutically acceptable adjuvant, this adjuvant is chosen from co-solvents, stabilizers, cryoprotective agents, desiccants, fillers. Without any limitation being implied, the co-solvents and the solubilizing agents are preferably chosen from polyethylene glycols (e.g. polyethylene glycols 300 and 400), propylene glycol, ethanol and surfactants such as, for example, polysorbate 80 or polyoxyethylenated derivatives (cremophors); the fillers and cryoprotective agents are preferably chosen from simple sugars, for example, glucose, mannitol, fructose or sorbitol, disaccharides, for example, sucrose, lactose, trehalose or maltose; or water-soluble polymers, for example dextrans, carboxymethylcellulose, polyvinylpyrrolidone or gelatine;

And the stabilizers are preferably chosen from antioxidants (e.g. ascorbic acid, acetylcysteine, sulphurous acid salts, monothioglycerol). Excipients used in parenteral formulations are described by Y. Mehmood et al, Open Science Journal of Pharmacy and Pharmacology, 2015, 3(3), 19-27 and R. G. Strickley, Pharmaceutical Research, Vol 21, No 2, 201-230.

The human dose of BC-3781 in buffered formulations will be between 10 mg and 1000 mg, preferably between 15 mg and 500 mg, most preferable between 25 mg and 300 mg e.g. 150 mg. Optionally the formulation can be administered several times a day e.g. BID, TID depending on the treatment requirement. The volume of administration can vary from 10 ml to 1000 ml, preferably 20 ml to 500 ml, most preferably between 20 ml to 300 ml e.g. 250 or 300 ml in adults.

In a preferred embodiment of the formulation according to the present invention, the buffer is 10 mM to 20 mM citrate buffer, the pH-value of the formulation is from 3 to 5.5, preferably pH 5, the concentration of BC-3781 is between 0.2 to 3 mg/ml (calculated as free base form), and the formulation comprises a pharmaceutically acceptable vehicle.

In a further preferred embodiment, the buffer is 10 mM citrate buffer, the pH-value of the formulation is from 3 to 5.5, preferably pH 5, the concentration of BC-3781 is between 0.3 to 1.2 mg/ml (calculated as free base form), and the formulation comprises a pharmaceutically acceptable vehicle.

In a further preferred embodiment, the buffer is 10 mM citrate buffer, the pH-value of the formulation is from 3 to 5.5, preferable pH 5, the concentration of BC-3781 is between 0.3 to 0.6 mg/ml (calculated as free base form) and the formulation comprises a pharmaceutically acceptable vehicle.

It is understood that the presentation kits for the formulation of BC-3781 optionally with adjuvants also fall within the context of the present invention. Presentation kits of any form can be suitable.

For example, the buffer can be presented in a glass vial optionally as buffer concentrate solution for further dilution, preferably in a pharmaceutically acceptable intravenous vehicle. The buffer concentrate can be diluted into commercially available infusion bags or bottles filled with a pharmaceutically acceptable intravenous vehicle to the desired molarity. BC-3781 is added as concentrate solution to the desired concentration or dose.

Alternatively, the buffer concentrate may be used to fill empty infusion bags (e.g. EVA bags), diluted with a pharmaceutically acceptable intravenous vehicle to the desired molarity and finally BC-3781 is added as solution or solid compound at the desired concentration.

Moreover, the buffer can be presented in an infusion bag or infusion bottle at the selected molarity, preferably in a pharmaceutically acceptable intravenous vehicle, for reconstitution of BC-3781 BC-3781 can be added e.g. as solution into the buffered infusion bags/bottles.

Alternatively, BC-3781 can be presented as a lyophilisate or concentrate solution in a glass vial for further dilution into the buffer vehicle, preferably both based in a pharmaceutically acceptable intravenous vehicle.

Furthermore, the presentation kits may encompass Ready to Use infusion bags and bottles containing the buffer, a pharmaceutically acceptable intravenous vehicle, optionally an adjuvant and BC-3781.

Sterile formulations of the present invention e.g. suitable inter alia for human administration can be prepared by known methods commonly used e.g. sterile filtration, sterile filtration and aseptically filling, heat sterilization or gamma radiation. The selected method will depend on the stability of the compound or solution to be sterilized e.g. preferred methods for sterilizing the buffer solutions in pharmaceutically acceptable intravenous vehicle without BC-3781 are sterile filtered followed by heat sterilization. Solutions containing BC-3781 are preferably sterile filtered followed by aseptical filling into the appropriate container e.g. glass vial, glass bottle, infusion bag.

In all the above mentioned embodiments, the pharmaceutically acceptable vehicle is preferably NSS, LRS and/or D5W, most preferred NSS.

Furthermore, in all the above mentioned embodiments, BC-3781 is preferably employed as a pharmaceutically acceptable salt, in particular as acetate and/or L-lactate, particularly preferred as acetate.

A further aspect of the present invention relates to a formulation according to the present invention for use in the treatment of diseases mediated by microbes.

In a preferred embodiment, the formulation is administered via intravenous application.

Furthermore, the present invention relates to a pharmaceutical presentation form comprising the injectable formulation according the present invention.

Furthermore, the present invention relates to a method of treatment of diseases mediated by microbes wherein a formulation according to the present invention is administered to a subject in need thereof.

In the method according to the present invention, the formulation is preferably administered via intravenous application.

The intravenous application includes bolus, slow bolus and infusion administration including continuous infusion.

The following abbreviations are used:

| | |
|---|---|
| API | Active pharmaceutical ingredient |
| BID | bis in die (twice a day) |
| EP | European Pharmacopoeia |
| g | gram |
| JP | Japanese Pharmacopoeia |
| kg | kilogram |
| l | liters |
| M | molar |
| mM | millimolar |
| min | minutes |
| ml | milliliters |
| NF | National formulary |
| q.s. | quantum satis |
| TID | ter in die (three times a day) |
| USP | Unites States Pharmacopoeia |
| w/v | weight/volume |

EXAMPLES

The excipients used to prepare clinical (human) formulations or components thereof are of Pharmacopoeial grade, e.g. USP and/or EP, and/or NF and/or JP.

Example 1

Preparation of 14-O-{[(1R, 2R, 4R)-4-amino-2-hydroxy-cyclohexylsulfanyl]-acetyl}-mutilin (BC-3781) formulations used to investigate tolerability in a rat dorsal tail vein model a) Preparation/Purchase of Pharmaceutical Vehicle Preparation of the pharmaceutical vehicle NSS is established by dissolving NaCl 0.9% (w/v). D5W is purchased from Fresenius Kabi.

b) Preparation of Buffer Solutions

| | |
|---|---|
| 20 mM Citrate buffer pH 5.0 (0.9% (w/v) NaCl): | 1.05 g citric acid in 250 ml 0.9% (w/v) NaCl adjusted with NaOH to pH 5.0 |
| 20 mM Citrate buffer pH 6.0 (0.9% (w/v) NaCl): | 1.05 g citric acid in 250 ml 0.9% (w/v) NaCl adjusted with NaOH to pH 6.0 |
| 20 mM Citrate buffer pH 7.0 (0.9% (w/v) NaCl): | 1.05 g citric acid in 250 ml 0.9% (w/v) NaCl adjusted with NaOH to pH 7.0 |
| 10 mM Citrate buffer pH 5.0 (0.9% (w/v) NaCl): | 1 ml of 20 mM citric acid buffer (0.9% (w/v) NaCl) + 1 ml 0.9% (w/v) NaCl |
| 20 mM Citrate buffer pH 5.0 (5% (w/v) Dextrose): | 1.05 g citric acid in 250 ml 5% (w/v) dextrose adjusted with NaOH to pH 5.0 |
| 20 mM Citrate buffer pH 7.0 (5% (w/v) Dextrose): | 1.05 g citric acid in 250 ml 5% (w/v) dextrose adjusted with NaOH to pH 7.0 |
| 20 mM citrate buffer pH 4.5 (0.9% (w/v) NaCl): | 1.05 g citric acid in 250 ml 0.9% (w/v) NaCl adjusted with NaOH to pH 4.5 |
| 100 mM citric acid monohydrate | 2.10 g citric acid dissolved in 100 ml $H_2O$ |
| 200 mM $Na_2HPO_4 \times 2H_2O$ | 3.56 g $Na_2HPO_4 \cdot 2H_2O$ dissolved in 100 ml $H_2O$ |
| 100 mM citrate/phosphate buffer pH 5.0 | 49 ml 100 mM citric acid monohydrate + 51 ml 200 mM $Na_2HPO_4 \times 2H_2O$ |
| 20 mM citrate/phosphate buffer pH 5.0 0.7% (w/v) NaCl | 5 ml 100 mM citrate/phosphate buffer pH 5.0 diluted with 0.9% (w/v) NaCl to 25 ml. | c) Final Preparation of Formulations

The test compound 14-O-{[(1R, 2R, 4R)-4-amino-2-hydroxy-cyclohexylsulfanyl]-acetyl}-mutilin (BC-3781), present as pharmaceutically acceptable salt, e.g. acetate or L-lactate, is dissolved in the buffer solutions, NSS or D5W to achieve a concentration of 6 mg/ml (calculated as free base form) For example, the following amounts are weighed in:

| Amount BC-3781 free base [mg] | Buffer Volume [ml] |
|---|---|
| 300 | 50.0 |
| 150 | 25.0 |

Example 2

Formulation preparation used in clinical phase 1 studies to investigate local tolerance differences—preparation of 10 mM citrate buffer normal saline formulations of BC-3781, normal saline formulations of BC-3781 and respective drug vehicles (in the following also referred to as "placebo formulations" or "placebo")

a) BC-3781 Concentrate Solution in Normal Saline

Preparation of BC-3781 solution was achieved by dissolving BC-3781 acetate in water for injection and additionally dissolving NaCl. After sterile filtration the solution was subsequently filled into vials under aseptic conditions.

Quantitative composition of BC-3781 saline vials

| Component | Amount |
|---|---|
| BC-3781.Ac | 150 mg free base |
| Sodium chloride | 0.135 g |
| Water for injection | to 15 ml |

Other preferred crystalline salts of BC-3781 are disclosed in WO 2011/146954.

b) Citrate Buffer Concentrate Solutions

The citrate buffer solution is prepared separately. Citric acid and trisodium citrate are dissolved in water for injection and subsequently filled into vials.

Batch formula of 250 mM citrate buffer concentrate solution

| Component | Amount per batch |
|---|---|
| Citric acid monohydrate | 16.8 g |
| Trisodium citrate dihydrate | 50.0 g |
| Water for injection | To 1000 ml |

The citrate buffer concentrate solution is filled into 10 ml vials under sterile conditions (e.g. sterile filtration, autoclaving).

Qualitative and quantitative composition of 250 mM citrate buffer vials

| Component | Content |
|---|---|
| Citric acid monohydrate | 0.168 g |
| Trisodium citrate dihydrate | 0.500 g |
| Water for injection | To 10 ml |

Alternatively the citrate buffer is prepared at a different molarity.

Batch formula of 540 mM citrate buffer concentrate solution

| Component | Amount per batch 540 mM concentrate |
|---|---|
| Citric acid monohydrate | 183.0 g |
| Trisodium citrate dihydrate | 538.0 g |
| Water for injection | To 5000 ml |

The citrate buffer concentrate solution is filled into 5 ml vials under sterile conditions (e.g. sterile filtration, autoclaving).

Quantitative compositions of citrate buffer vials

| Component | Content 540 mM concentrate |
|---|---|
| Citric acid monohydrate | 0.183 g |
| Trisodium citrate dihydrate | 0.538 g |
| Water for injection | to 5 ml | c) Clinical Formulations

Depending on the required volume and concentration of the BC-3781 infusion solution, sterile bags are filled with the required amounts of i) BC-3781 concentrate solution in normal saline (preparation described in Example 2a)), ii) citrate buffer concentrate solution (preparation described in Example 2b) and iii) commercially available NSS.

Amounts of infusate components used in the preparation clinical formulations using 250 mM citrate buffer concentrate to prepare the BC-3781 citrate buffer formulations are shown in the table below. In addition the table also lists the preparation of the BC-3781 reference formulation in NSS and NSS-placebo formulations.

| Final BC-3781 concentration/ volume | Formulation Vehicle | Overall Volume [ml] | Commercial 0.9% (w/v) saline [ml] | 250 mM Citrate buffer concentrate [ml] | BC-3781 concentrate [ml] |
|---|---|---|---|---|---|
| 400 mg/200 ml | 0.9% (w/v) saline | 250 | 200 | — | 50 |
|  | citrate buffered 0.9% (w/v) saline[#] | 250 | 190 | 10 | 50 |
| 0 mg/ml (250 ml Placebo) | 0.9% (w/v) saline | 250 | 250 | — | — |
| 150 mg/400 ml | citrate buffered 0.9% (w/v) saline[#] | 500 | 461.25 | 20 | 18.75 |
| 200 mg/400 ml | citrate buffered 0.9% (w/v) saline[#] | 500 | 455 | 20 | 25 |
| 0 mg/ml (500 ml Placebo) | 0.9% (w/v) saline | 500 | 500 | — | — |

[#]The pH of the resulting infusates is about 5.

Amounts of infusate components used in the preparation of clinical formulations using 540 mM citrate buffer concentrate to prepare the BC-3781 citrate buffer formulation are shown in the table below. In addition, the table also lists the preparation of the BC-3781 reference formulation in normal saline and the normal saline placebo formulation.

| Final BC-3781 concentration/ volume | Formulation Vehicle | Overall Volume [ml] | Commercial normal saline solution* [ml] | 540 mM citrate buffer concentrate [ml] | 10 mg/ml BC-3781 concentrate [ml] |
|---|---|---|---|---|---|
| 150 mg/270 ml | 0.9% (w/v) saline | 270 | 255 | — | 15 |
| 150 mg/270 ml | citrate buffered 0.9% (w/v) saline# | 270 | 250 | 5 | 15 |
| 0 mg/ml (Placebo) | 0.9% (w/v) saline | 270 | 270 | — | — |

*commercially available sterile NaCl solution, e.g. Ecobags;
The pH of the resulting infusate is about 5.

The infusate components of the clinical formulations are filled into commercially available sterile empty infusion bags e.g. 300 ml or 500 ml EVA bags.

Alternatively the formulation can also be reconstituted by adding the required amounts of BC-3781 concentrate solution presented in Example 2a) and the buffer concentrate solution presented in Example 2b) to commercially prefilled normal saline infusion bags. Optionally, the volume of added BC-3781 concentrate and citrate buffer concentrate solution is withdrawn from the commercial normal saline infusion bags before the addition.

The clinical formulations described in the tables above have been used to evaluate the local tolerance differences of BC-3781 normal saline with BC-3781 normal saline citrate buffer formulation. The citrate buffered normal saline formulations have shown superior local tolerance compared to normal saline formulations.

Specifically the two following different BC-3781 formulations 150 mg BC-3781 normal saline formulation in 270 ml infused over 1 h 150 mg BC-3781 normal saline citrate buffer formulation in 270 ml infused over 1 h have been investigated in a randomized, double blind placebo controlled clinical phase 1 study.

Example 3

The formulation can also be prepared by directly dissolving BC-3781 salt, NaCl, citric acid, trisodium citrate in water. Subsequently this formulation can be filled into appropriate containers e.g. infusion bags, infusion bottles under aseptic conditions. The pH of the formulation is about 5 and can be adjusted with either HCl or NaOH to be exactly 5.0 if required.

Batch Formula of Ready to Use (RTU) Infusion Bag

| Component | Concentration (g/l) | Per dose (g/250 ml) |
|---|---|---|
| BC-3781.Ac. | 0.60* | 0.175 |
| Sodium Chloride | 9.000 | 2.2500 |
| Citric Acid Anhydrous | 0.615 | 0.1537 |

-continued

| Component | Concentration (g/l) | Per dose (g/250 ml) |
|---|---|---|
| Tri-sodium Citrate Dihydrate | 2.000 | 0.5000 |
| Water for injection | q.s. to volume | q.s. to 250 ml |

*Amount of BC-3781 acetate salt is higher and will depend on potency (free base content) of API. However, formulation concentration is 0.60 g/l BC-3781 free base.

Example 4

The formulation can also be prepared by separate preparation of the BC-3781 concentrate solution filled into vials and drug free citrate buffer normal saline bags.

BC-3781 concentrate solution is prepared as described in Example 2 step a).

The buffer solution is prepared separately, filtered through 0.45 μm cartridges for retention of bacteria and particles and filled into appropriate containers e.g. infusion bags or infusion bottles. The pH is about 5.

Batch formula for citrate buffered saline bags

| Component | Function | Amount/batch | Amount/bag |
|---|---|---|---|
| Citric acid anhydrous | Buffer acid | 2829 g | 166 mg |
| Trisodium citrate dihydrate | Buffer salt | 9200 g | 0.54 g |
| Sodium chloride | Tonicity modifier | 41.4 kg | 2.43 g |
| Water for injection | Solvent | To 4600 l | To 270 ml |

The resulting buffer containers are heat sterilized.

Finally the content of the BC-3781 concentrate vial is diluted (reconstituted) into the citrate buffer infusion bag yielding the final formulation. The resulting BC-3781 formulation corresponds to 150 mg of BC-3781 in 10 mM citrate buffer normal saline with a pH of about 5.

Example 5

Preparation of citrate buffer concentrate vial containing BC-3781 acetate for reconstitution into commercial available normal saline bags.

a) Preparation of 150 mM Citrate Buffer Solution

Preparation of the buffer 150 mM concentrates was done by dissolving appropriate amounts of citric acid monohydrate with trisodium citrate dihydrate in water. The resulting al is about 5.

| | 150 mM Citrate Buffer |
|---|---|
| Citric acid monohydrate | 48 mM (10084.8 mg/l) |
| Trisodium citrate dihydrate | 102 mM (29998.2 mg/l) | b) Preparation of BC-3781 Acetate Concentrate Solution in 150 mM Citrate Buffer 150 mg free base equivalent of BC-3781 acetate is dissolved in 20 ml of 150 mM citrate buffer resulting in a concentration of 7.5 mg/ml. The solution can be filled into e.g. glass vials.

Reconstitution of 20 ml of above solution in e.g. 250 ml commercial saline infusion bag or bottle will result in 150 mg BC-3781 free base in about 10 mM citrate buffer with a pH about 5.

Buffered formulations of the present invention have been investigated in vivo in a rat tail model as well as in a human clinical study. The test condition details and the surprising results are presented in the following paragraphs.

Description of the Rat Tail Model to Evaluate the Local Tolerabilities:

A site of infusion tolerability model for infusion of BC-3781 into the rat dorsal tail vein was developed to investigate potential intravenous clinical formulations of BC-3781. For this, female Sprague Dawley (SD) rats were catheterized with a permanent venous catheter (BD®, G21) and the different formulations of BC-3781 at a concentration of 6 mg/ml were infused with a fixed infusion rate of 1 ml/min to a final dose of 75 mg/kg. Plasma and urine were checked for signs of hemolysis between 5 to 30 min. The local tolerance at site of infection (tail vein) was checked 24 h post application. The developed score system together with the information on hemolysis in plasma and/or urine was collected and used for analysis.

The tested infusion formulations were ranked according to their scores. The buffered infusion solution of BC-3781 showed improved local tolerability, and for buffered formulations below pH 7 no hemolysis was observed, both effects being compared to the reference formulation in saline (NSS) and D5W.

Performing the Test and Results:

a) Local Tolerability Model

To determine the local tolerability of intravenous formulations a rat tail vein infusion model was developed to test formulations for BC-3781 prepared according to Example 1. For this, a score system was employed to describe the clinical signs at the site of injection.

An optical check of the dorsal tail vein 24 h after infusion was defined as time point for read out. The following scores have been applied:

| no abnormality observed of the rat tail vein after 24 h was rated | 0 points |
|---|---|
| slight red spots (ecchymosis) | 1 point |
| moderate spots | 2 points, |
| and more severe blue-dark red spots were counted as | 3 points. |

In case of death 3 points were calculated.

As reference formulation, BC-3781 dissolved in NSS or D5W (with no buffer) prepared according to Example 1 was used. In order to discriminate between the formulations, an infusion of NSS and D5W formulation under conditions as described above caused detectable hemolysis and moderate local irritation of the infusion site. All formulations were delivered as blinded samples to the animal test site. Unblinding of formulations was done at the end of the study.

b) Blood Collection

Blood was withdrawn from the sublingual vein 15 min after end of infusion, centrifuged at 2 g at 4° C. for 5 minutes. Plasma was collected and checked visually for signs of hemolysis and stored afterwards at −20° C. To evaluate the impact on pharmacokinetics (PK) of various formulations, the plasma concentrations of BC-3781 were determined and compared.

c) Urine

After end of infusion the anesthesia was removed and animals were kept single caged on white tissue sheets during recovery from anesthesia. Observed slight erythroid urine drops on the tissue were recorded as sign of hemolysis.

d) Data Analysis

Scores from the local tolerance model for each formulation were summed up and then divided by the corresponding number of animals (n=3-12). In addition, signs of hemolysis in plasma and urine were taken into account for the ranking of the formulations.

Results in the Rat Tail Model a) Formulations of BC-3781 Tested in the Rat Tail Vein Infusion Model

| Formulation | Composition of formulation* | Type |
|---|---|---|
| Formulation 0 (test set up) | 6 mg/ml BC-3781.Ac in 0.9% (w/v) NaCl | Reference formulation |
| Formulation 1 | 6 mg/ml BC-3781.Ac in 0.9% (w/v) NaCl | Reference formulation |
| Formulation 2 | 6 mg/ml BC-3781.Ac in 5% (w/v) dextrose | Reference formulation |
| Formulation 3 | 6 mg/ml BC-3781.Ac in 0.9% (w/v) NaCl | Reference formulation |
| Formulation 5 | 10 mM citrate buffer pH 5.0 in 0.9% (w/v) NaCl (placebo formulation) | Placebo formulation |
| Formulation 7 | 6 mg/ml BC-3781.Ac in 0.9% (w/v) NaCl | Reference formulation |
| Formulation 8 | 6 mg/ml BC-3781.Ac in 5% (w/v) dextrose | Reference formulation |
| Formulation 9 | 6 mg/ml BC-3781.Ac in 10 mM citrate buffer pH 5.0 in 0.9% (w/v) NaCl | Buffered formulation |
| Formulation 12 | 6 mg/ml BC-3781.La in 20 mM citrate buffer pH 5.0 in 0.9% (w/v) NaCl | Buffered formulation |
| Formulation 13 | 6 mg/ml BC-3781.Ac in 20 mM citrate buffer pH 5.0 in 0.9% (w/v) NaCl | Buffered formulation |
| Formulation 14 | 6 mg/ml BC-3781.La in 20 mM citrate buffer pH 5.0 in 0.9% (w/v) NaCl | Buffered formulation |
| Formulation 19 | 6 mg/ml BC-3781.Ac in 20 mM citrate buffer pH 5.0 in 5% (w/v) dextrose | Buffered formulation |
| Formulation 20 | 6 mg/ml BC-3781.Ac in 20 mM citrate buffer pH 5.0 in 0.9% (w/v) NaCl | Buffered formulation |
| Formulation 22 | 6 mg/ml BC-3781.Ac in 20 mM citrate buffer pH 4.5 in 0.9% (w/v) NaCl | Buffered formulation |
| Formulation 30 | 6 mg/ml BC-3781.Ac in 20 mM citrate/ phosphate buffer 0.7% (w/v) NaCl pH 5.0 | Buffered formulation |
| Formulation 37 | 6 mg/ml BC-3781.Ac in 20 mM citrate buffer pH 6.0 in 0.9% (w/v) NaCl | Buffered formulation |
| Formulation 38 | 6 mg/ml BC-3781.Ac in 20 mM citrate buffer pH 7.0 in 0.9% (w/v) NaCl | Buffered formulation |
| Formulation 39 | 6 mg/ml BC-3781.Ac in 20 mM citrate buffer pH 5.0 in 5% (w/v) dextrose | Buffered formulation |
| Formulation 40 | 6 mg/ml BC-3781.Ac in 20 mM citrate buffer pH 7.0 in 5% (w/v) dextrose | Buffered formulation |

*the concentration of 6 mg/ml relates to BC-3781 free base content

Formulation Preparation

The preparation of the formulations is described in Example 1. In the active formulations the required amount of BC-3781 present either as acetate or L-lactate salt was dissolved in the respective in the buffer solutions, NSS or D5W as listed in table above. After complete dissolution the required dilutions were immediately administered to the animals. 75 mg/kg BC 3781 dose refer to the free base content of BC-3781.

b) Specifications and Source of the Animals

| Test animal | Rat, Sprague Dawley (SD) |
| Supplier | Charles River Deutschland GmbH, D-97633 Sulzfeld |
| Sex | Female |
| Body weights | 200-240 g | c) Infusion Setting

The dorsal tail vein was cannulated using a permanent venous catheter (BD Insyte™, 24GA) after heating the tail under a heating lamp for 5 min. After cannulation rats were anesthetized using isoflurane in a concentration of 5% to initiate and 3.5% for maintenance of narcosis (mask). Via a programmable syringe pump, various BC-3781 formulations were infused into the cannulated rat dorsal tail vein (1 ml/min, 6 mg/ml, about 2 min). After end of infusion, the catheter were flushed with 0.1-0.2 ml saline. Catheter and syringe were disposed and the connecting tubing was rinsed with ethanol and dried for re-usage. The group size per infusion setting was 3.

Results of Tested Formulations in in the Rat Tail Model (Local Tolerance Score and Hemolysis in Plasma and Urine)

| Formulation | Active/Placebo | Dead | N* | Score/n |
|---|---|---|---|---|
| 5 | P* | 0% | 3 | 0 |
| 0, 1, 3, 7 | A | 0% | 12 | 1.5 |
| 2, 8 | A | 0% | 6 | 2 |
| 9 | A | 0% | 3 | 1.0 |
| 12, 14 | A | 0% | 6 | 1.17 |
| 13, 20 | A | 0% | 6 | 0.67 |
| 22 | A | 0% | 3 | 1 |
| 37 | A | 0% | 3 | 0.33 |
| 38 | A | 0% | 3 | 1 |
| 30 | A | 0% | 3 | 0.66 |
| 19, 39 | A | 0% | 3 | 1.33 |
| 40 | A | 0% | 3 | 0 |

*Legend:
A active;
P placebo;
N is number of tested animals

The test results confirm the surprising effect of BC-3781 buffered solutions. All tested buffered solutions exhibit a better tolerability score when compared to the non-buffered reference formulations. Surprisingly, in addition no hemolysis is observed for the buffered BC-3781 solutions, whereas non buffered solution or buffered solutions at pH 7 do cause hemolysis observable in plasma and urine. These surprising effects cannot be linked to limited solubility of BC-3781 at blood pH nor could the effect be caused by limited stability of BC-3781 at physiological pH (about pH 7).

Results of a Clinical Phase 1 Study

The improved local tolerability of BC-3781 buffered formulations was also confirmed in a clinical phase 1 study, comparing formulations of BC-3781 in NSS (150 mg BC-3781 in 270 ml) with BC-3781 in citrate buffered saline (150 mg BC-3781 in 270 ml), prepared according to Example 2. The study was randomized, double blind and placebo controlled (using normal saline as placebo). In total 60 healthy subjects were treated—25 males and 35 females. The primary endpoint of the study was moderate pain and erythema within the first 3 days. The formulations were infused over 1 h and surprisingly the occurrence of moderate pain and/or erythema during the first 3 days was approximately halved when lefamulin was administered in citrate buffered saline. For example from a total of 150 infusions in the normal saline arm 13 infusions (8.7%) caused moderate pain whereas in the citrate buffered saline arm only 6 of 150 infusions (4%) where associated with moderate pain.

What is claimed is:

1. An injectable pharmaceutical formulation comprising a compound of formula (I)

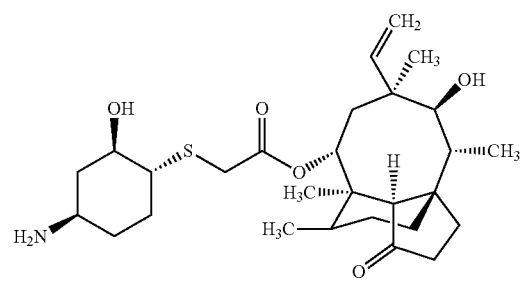

or a pharmaceutically acceptable salt thereof, said formulation being buffered to a pharmaceutically acceptable pH-value of from 4 to 6, wherein the buffer is a citrate buffer.

2. The formulation according to claim 1, wherein the buffered formulation comprises a pharmaceutically acceptable vehicle.

3. The formulation according to claim 1, wherein the citrate buffer is 10 mM to 20 mM, the pH-value of the formulation is from 4 to 5.5, the concentration of the compound of formula (I) is between 0.2 to 3 mg/ml (calculated as free base form), and the formulation comprises a pharmaceutically acceptable vehicle.

4. The formulation according to claim 3, wherein the citrate buffer is 10 mM and the concentration of the compound of formula (I) is between 0.3 to 1.2 mg/ml.

5. The formulation according to claim 4, wherein the concentration of the compound of formula (I) is between 0.3 to 0.6 mg/ml.

6. The formulation according claim 1, wherein the compound of formula (I) is employed as a pharmaceutically acceptable salt.

7. A method of treating diseases mediated by microbes comprising administering the formulation according to claim 1 to a subject in need of said treatment.

8. The method according to claim 7, wherein the formulation is administered via intravenous application.

9. A pharmaceutical composition, comprising an injectable formulation comprising a compound of formula (I),

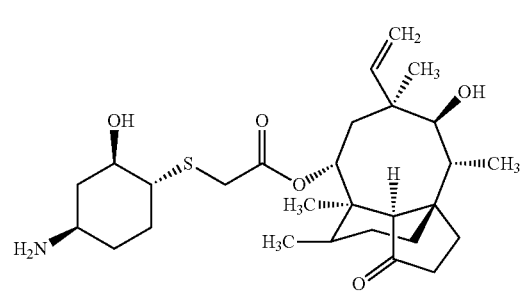

or a pharmaceutically acceptable salt thereof, said formulation being buffered to a pharmaceutically acceptable pH-value of from 4 to 5.5, wherein the buffer is a citrate buffer.

10. The injectable pharmaceutical formulation according to claim 1, wherein the pharmaceutically acceptable pH-value is from 4 to 5.5.

11. The injectable pharmaceutical formulation according to claim 10, wherein the pharmaceutically acceptable pH-value is from 4 to 5.

12. The injectable pharmaceutical formulation according to claim 1, wherein the pharmaceutically acceptable pH-value is about 5.

13. The formulation according to claim 1, wherein the citrate buffer is a 10 to 20 mM citrate buffer.

14. The formulation according to claim 13, wherein the citrate buffer is a 10 mM citrate buffer.

15. The formulation according to claim 2, wherein the pharmaceutically acceptable vehicle is selected from the group consisting of normal saline solution, 5% dextrose solution and mixtures thereof.

16. The formulation according to claims 3, 4 or 5, wherein the pH-value of the formulation is 5.

17. The formulation according claim 6, wherein the pharmaceutically acceptable salt is selected from the group consisting of acetate and L-lactate.

\* \* \* \* \*